(12) United States Patent
Garton et al.

(10) Patent No.: US 8,288,596 B2
(45) Date of Patent: *Oct. 16, 2012

(54) MANUFACTURE OF PURIFIED ALCOHOLS

(75) Inventors: Ronald Dean Garton, Wezembeek-Oppem (BE); Corey W. Reed, Baton Rouge, LA (US); Krishna Kulai Rao, The Woodlands, TX (US); Bruce D. Lilly, Prairieville, LA (US); Ramzi Yanni Saleh, Baton Rouge, LA (US); Raphael Frans Caers, Edegem (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 388 days.

This patent is subject to a terminal disclaimer.

(21) Appl. No.: 12/531,759

(22) PCT Filed: Feb. 27, 2008

(86) PCT No.: PCT/EP2008/001660
§ 371 (c)(1),
(2), (4) Date: Feb. 2, 2010

(87) PCT Pub. No.: WO2008/116542
PCT Pub. Date: Oct. 2, 2008

(65) Prior Publication Data
US 2010/0137630 A1    Jun. 3, 2010

(51) Int. Cl.
*C07C 29/88* (2006.01)
*C07C 27/74* (2006.01)

(52) U.S. Cl. ........ 568/913; 568/918; 568/591; 568/594; 568/605

(58) Field of Classification Search ................. 568/913, 568/918, 591, 594, 605
See application file for complete search history.

(56) References Cited

U.S. PATENT DOCUMENTS

| | | | |
|---|---|---|---|
| 2,519,540 A | 8/1950 | Bramwyche et al. | |
| 2,668,862 A | 2/1954 | Price, Jr. | |
| 3,819,728 A | 6/1974 | Kwantes et al. | |
| 6,015,875 A | 1/2000 | Smith, Jr. et al. | |
| 6,214,172 B1 | 4/2001 | Gröning et al. | |
| 6,518,464 B2 | 2/2003 | Therre et al. | |

FOREIGN PATENT DOCUMENTS

| | | |
|---|---|---|
| GB | 753218 | 7/1956 |
| GB | 820475 | 9/1959 |
| WO | WO2008/116542 | 10/2008 |

OTHER PUBLICATIONS

V.M.T.M. Silva et al., "Novel Process for Diethylacetal Synthesis," AIChE Journal, vol. 51, No. 10, (Oct. 2005) pp. 2752-2768.
G.K. Gandi et al, "Process Development for Dimethylacetal Synthesis: Thermodynamics and Reaction Kinetics," Ind. Eng. Chem. Res (2005), No. 44, pp. 7287-7297.

*Primary Examiner* — Sikarl Witherspoon
(74) *Attorney, Agent, or Firm* — Leandro Arechederra, III; Andrew B. Griffis

(57) ABSTRACT

Acetals are formed from an aldehyde hydrogenation product mixture comprising alcohols and at most 2% of alde-hydes and the product is distilled to yield purified alcohols and a second stream containing acetals and/or unsaturated ethers.

20 Claims, 2 Drawing Sheets

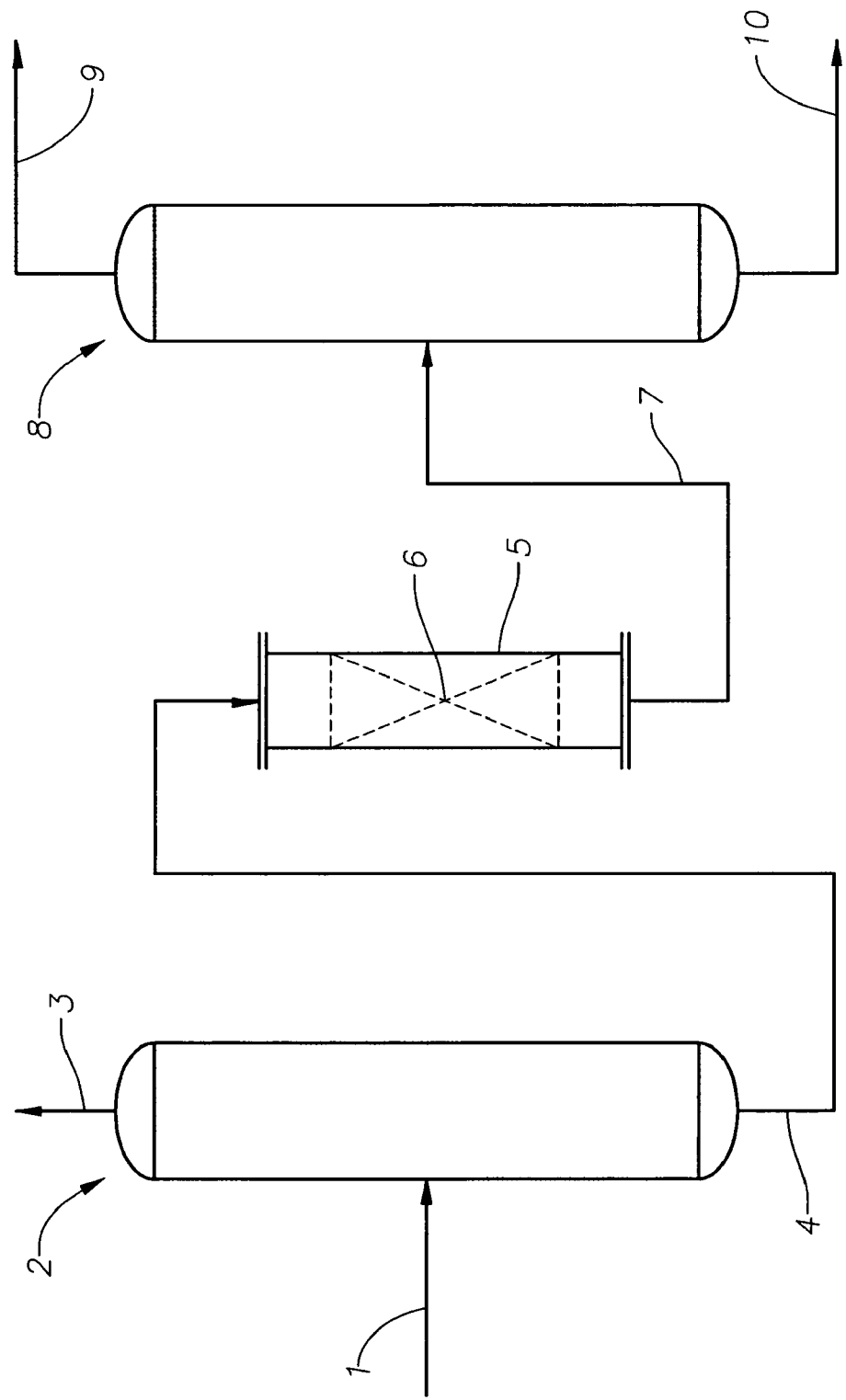

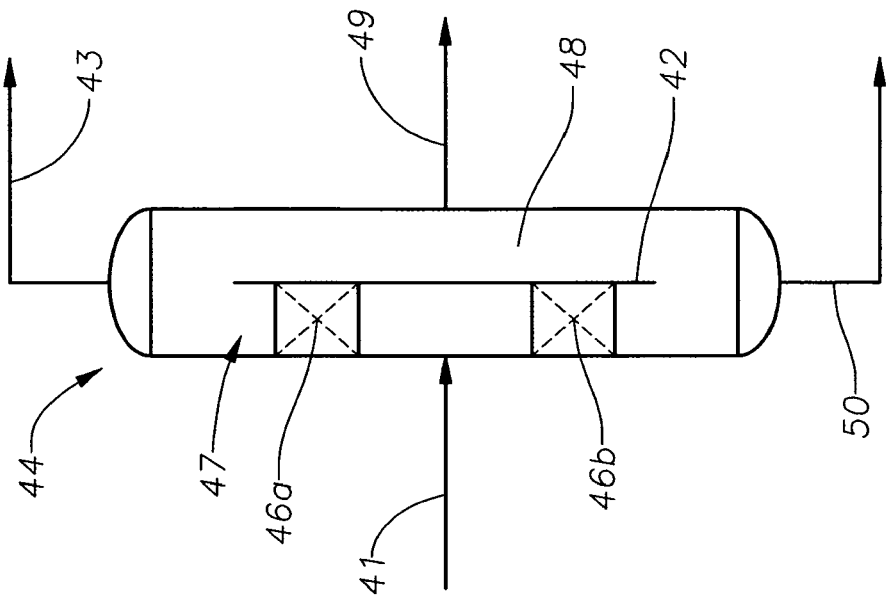
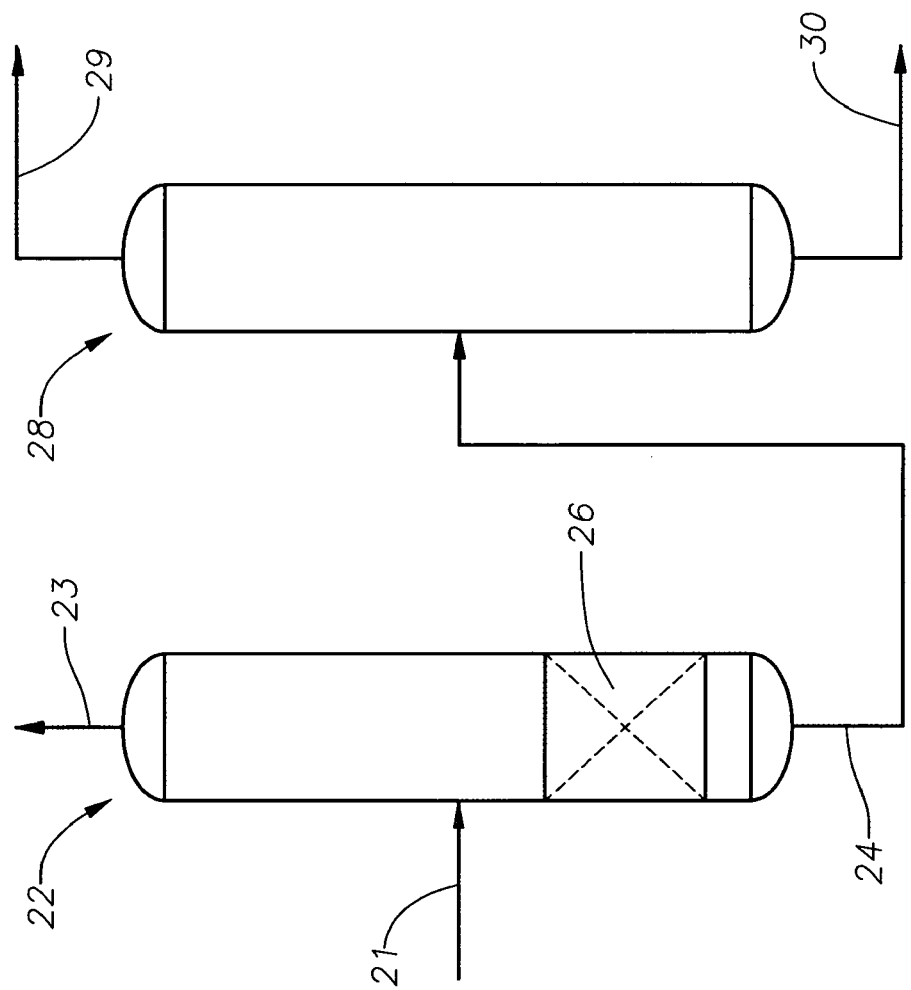

MANUFACTURE OF PURIFIED ALCOHOLS

CROSS REFERENCE TO RELATED APPLICATIONS

This application is a 371 National Stage Application of International Application No. PCT/EP2008/001660, filed Feb. 27, 2008, which claims the benefit of U.S. application Ser. No. 11/728,854, filed Mar. 27, 2007, the disclosures of which are herein incorporated by reference in their entireties.

FIELD OF THE INVENTION

The invention relates to the manufacture of purified alcohols by the hydroformylation (Oxo) reaction, in particular to the purification of Oxo alcohols produced by the hydrogenation of aldehydes.

BACKGROUND OF THE INVENTION

The hydroformylation reaction, also known as the Oxo Reaction or Oxo Process, consists in reacting a synthesis gas made up of a mixture of carbon monoxide and hydrogen and at least one $C_nH_{2n}$ olefin so as to obtain an aldehyde product containing n+1 carbon atoms. The oxonation reaction is generally catalyzed with carbonyls of transition metals such as cobalt or rhodium, optionally in presence of a ligand to stabilize the carbonyl complex of the metal. The aldehyde may then be catalytically hydrogenated to the corresponding alcohol, but optionally some or most of the aldehyde may be separated off for use as such or for conversion into higher molecular weight alcohols, as described below, or into carboxylic acids, optionally also those having the higher molecular weight. Such a process sequence of hydroformylation followed by hydrogenation may lead to the production of n-butanol, isobutanol, mixtures of C4 alcohols, n-pentanol, 2-methyl-butanol, 3-methyl butanol, mixtures of at least two C5 alcohols, or higher alcohols such as isoheptyl alcohol, iso-octyl alcohol, isononyl alcohol, isodecyl alcohol, isoundecyl alcohol, or isotridecyl alcohol. The Oxo Process, as well as its hydrogenation step, is described in detail in patents too numerous to recite. It is commercially highly important, producing products that find uses in plastics, soaps, lubricants, and other products.

Alternative processes for producing alcohols may start with the hydroformylation of lower carbon number olefins, such as ethylene, propylene and butenes to the corresponding aldehyde or aldehyde mixtures containing one more carbon number than the starting olefin or olefins, as already mentioned above. These aldehydes, or mixtures thereof, are then subjected to aldolisation to produce condensation products, typically higher aldehydes containing at least one extra carbon-carbon double bond, often referred to as enals. These enals or enal mixtures may be hydrogenated to the corresponding saturated aldehydes or aldehyde mixtures, or directly to the corresponding alcohols or alcohol mixtures. Examples of products produced by such processes are 2-methyl pentanol, 2-ethyl hexanol, 2,4-dimethyl heptanol and 2-propyl heptanol, but other alcohols and alcohol mixtures produced in this way are also known.

In conventional commercial processes, the desired alcohol fraction after the first hydrogenation section as part of the various processes as described above typically contains about 0.05 to about 0.5 weight % carbonyl-containing compounds, particularly aldehydes. The presence of such an amount of carbonyl-containing compounds generally leads to poor color and undesirable odors in derivatives, such as plasticizers, produced from the alcohols. The alcohol fraction is therefore generally subjected to hydrofinishing to reduce its carbonyl level. This is a problem because of the requirement of numerous additional reaction steps along with attendant apparatus. An alternative to hydrofinishing is to treat the alcohol with $NaBH_4$. This is a less complex process step, but the sensitivity of $NaBH_4$ to water introduces a safety risk that must be controlled. It would be highly beneficial if a process/system could be devised to eliminate these steps of reducing residual aldehyde, or to make the elimination of traces of aldehydes a more simple process, system or method.

The present inventors have surprisingly discovered that the formation of acetals and/or unsaturated ethers by the reaction of alcohols and aldehydes may be exploited to produce high purity alcohols and avoid some or all of the requirements of hydrofinishing or other carbonyl reduction steps.

The formation of acetals is the subject of numerous patents. Acetals are important as fragrances, pharmaceuticals, flavorings, and as oxygenated additives to reduce particulate and $NO_x$ emissions on the combustion of fuels.

In U.S. Pat. No. 2,519,540, acetaldehyde and ethanol are converted to diethyl acetal in the presence of an acidic catalyst, such as sulfuric acid or phosphoric acid, and inert diluent immiscible with water, such as kerosene, n-hexane, carbon tetrachloride, and the like. The acetal is recovered from the diluent phase by distillation.

U.S. Pat. No. 2,668,862 is directed to an improved process for producing and recovering higher molecular weight acetals. The alcohol and aldehyde are reacted in the presence of a catalyst such as (preferably) anhydrous hydrogen chloride at room temperature. Water formed during the reaction is absorbed by the addition to the reaction mixture of a dehydrating salt such as sodium sulfate or calcium chloride. The acetal product is isolated by adding an aqueous alcohol to the reaction product, causing the acetal to separate out as a bottom layer from which is can be drawn off after settling.

U.S. Pat. No. 6,015,875 produces acetals by the reaction of aldehydes and alcohols, separately added to a reaction distillation column, in the presence of a catalyst. The process includes the concurrent fractional distillation of the reaction mixture to separate the reaction products, acetal as overheads and water as bottoms.

U.S. Pat. No. 6,214,172 teaches preparation of methylglyoxal dimethyl acetal by reacting 2-oxopropanal with methanol in the presence of an acidic ion exchanger. The product acetal is obtained by azeotropic distillation with water, with the mixture separating at the top of the distillation column into an aqueous phase and acetal phase.

U.S. Pat. No. 6,518,464 relates to a process for preparing unsaturated acetals by reacting aliphatic olefins with allyl alcohols in a reaction column, where the reactants are only partially reacted in the reaction column. Vapor comprising alcohol and aldehyde are taken overhead from a reaction column and, after separation from water, are returned to the top of the reaction column as reflux. The acetal is removed as bottoms and then concentrated in two stages.

Silva and Rodrigues disclose the production of acetal catalyzed by an acid resin using simulated a moving-bed reactor. Acetaldehyde conversion is reported to be about 98%. See Silva et al., Novel Process for Diethylacetal Synthesis, AIChE Journal, Vol. 51, No. 10, pp. 2752-2768 (October 2005). A batch-scale comparison of the production of acetal by an acid resin and a zeolite catalyst was also reported by Gandi, Silva, and Rodrigues in Ind. Eng. Chem. Res. 2005, 44, 7287-7297.

However, as far as the present inventors are aware, the prior art has not purified the alcohol product of the Oxo Process by using the reaction of aldehydes and alcohols to make acetals and/or unsaturated ethers.

SUMMARY OF THE INVENTION

In an embodiment, the invention is directed to purification of the alcohol product of the Oxo Process by the reaction of alcohols and aldehydes to make the corresponding acetals and/or unsaturated ethers and then separating the desired alcohol from other products by distillation. The invention therefore provides a method for isolation and/or purification of an alcohol comprising the steps of
(i) catalytically hydrogenating an aldehyde containing stream to produce a first mixture comprising at most 2% wt of the aldehyde and at least 75% wt of the alcohol based on the weight of the total first mixture,
(ii) contacting the first mixture with an acetal formation catalyst under conditions suitable for formation of the acetal and/or an unsaturated ether of the aldehyde and the alcohol to produce a second mixture comprising the acetal and/or the unsaturated ether and the alcohol, and
(iii) distilling the second mixture to produce an overhead comprising the alcohol and a first bottoms comprising at least one of the acetal and the unsaturated ether.

In still another embodiment, the invention is directed to a distillation system for the purification of alcohols and/or the production of acetals and/or the production of unsaturated ethers, said system having at least one distillation tower comprising or associated with a catalytic distillation column. The invention therefore also provides a system comprising a hydrogenation reactor containing a catalyst effective for hydrogenating aldehydes to alcohols, a first distillation tower downstream of the hydrogenation reactor, the first distillation tower having an inlet, an outlet located substantially at or near the overhead of the tower and an outlet located substantially at or near the bottom of the tower, and an aldehyde elimination reactor, wherein the aldehyde elimination reactor comprises distillation packing and/or trays and a catalyst effective for converting an aldehyde and an alcohol to the corresponding acetal.

It is an object of the invention to treat a product stream comprising alcohols and aldehydes by contacting said stream with a catalyst suitable for the production of acetals, for the purpose of upgrading said stream to higher value products, such as purified alcohols, acetals, unsaturated ethers, or a combination thereof. Additional objects include the elimination of aldehydes from product streams, production of acetals, and/or production of unsaturated ethers.

These and other objects, features, and advantages will become apparent as reference is made to the following drawings, detailed description, preferred embodiments, examples, and appended claims.

BRIEF DESCRIPTION OF THE DRAWINGS

In the accompanying drawings, like reference numerals are used to denote like parts.

FIGS. 1-3 illustrate schematically some of the various embodiments of the invention.

DETAILED DESCRIPTION

According to the invention, a stream comprising one or more alcohols and one or more aldehydes is contacted under suitable conditions with a catalyst for the production of acetals and/or unsaturated ethers from aldehydes and alcohols. In embodiments the stream will comprise only residual amounts of aldehydes, meaning an excess of two equivalents of alcohol per aldehydes. In preferred embodiments the aldehyde will be present in the stream contacting the catalyst for the production of acetals in the amount of from 0.05 to 2 wt %, in embodiments 0.05 to 0.50 wt %, in other embodiments 0.1 wt % to 1.0 wt %, based on the weight of the entire stream. Additional embodiments include any of the aforementioned lower limits to any of the aforementioned upper limits, e.g., 0.1 wt % to 1.0 wt %. In embodiments the alcohol will be present in the amount of at least 75 wt %. In other embodiments the alcohol will be present in the amount of at least 95 wt %. The remainder may be various materials such as unreacted olefins, paraffins, heavier material such as acetals, ethers, esters, recycle or rerun material, cracked bottoms product, catalyst solution, and the like.

The stream comprising the one or more alcohols and one or more aldehydes advantageously comes from, but is not limited to, any process for the conversion of alpha-olefins (linear and/or branched) and/or internal olefins (linear and/or branched) to alcohols. Preferred processes include the Oxo Process as described above, including hydrogenation, or from a modified, single-step oxo process (the modified Shell process), or the low pressure Oxo (LPO) process, typically using a rhodium catalyst together with a ligand. Many ligands are known, and phosphines such as triphenylphospine (TPP), its oxide (TPPO) or phosphites have been described in numerous publications and are commercially used. The feedstocks for the Oxo process may be derived by the Octol™ process, Dimersol™ process, by Fisher-Tropsch synthesis, by the SHOP process, and so on. Such processes are per se well-known in the art. See for instance B. Elvers, et al., Ed., Ullmann's Encyclopedia of Chemical Technology, 5th Ed., Vol. A18, VCH Verlagsgesellschaft mbH, Weinheim, 1991, p. 321-327; or WO 2005058787 A1 and WO 2005058782 A1, and references cited therein.

It is preferred that the process of the invention be integrated with conventional hydroformylation processes. Conditions in the hydroformylation process may be conventional. The catalyst may be for example and in a preferred embodiment, cobalt-based and the operating temperatures, pressures and other conditions such as synthesis gas composition may be controlled in accordance with the usual expertise of the person skilled in the art to maximize yield of the desired higher alcohol product. In an embodiment the hydroformylation reaction may be carried out at a pressure of 150-300 atm, and a temperature of 120-190° C.

The oxo catalyst may be used in desired active form in predetermined amounts, for example cobalt in a concentration of from 0.05-3 wt %, preferably from 0.05-1.0 wt % as metal based on the weight of the olefinic feed. Typically the synthesis gas used might have a $H_2$:CO volume ratio in the range 0.9:1-1.5:1. The oxo catalyst is generally separated from the product mixture prior to the hydrogenation step. A stream rich in aldehyde may optionally also be withdrawn prior to hydrogenation.

In another preferred embodiment, the invention is integrated with the Low Pressure Oxo (LPO) process, more suitable for the hydroformylation of lower molecular weight olefins, such as ethylene, particularly propylene and butylenes, especially n-butenes such as butene-1 and in some embodiments also cis- and/or trans-butene-2, to produce the corresponding aldehydes. The LPO process is also suitable to hydroformylate higher molecular weight unbranched and terminal olefins such as pentene-1, hexene-1, heptene-1 or octene-1. The LPO process prefers to use rhodium as the hydroformylation catalyst, and prefers to operate at a pressure of less than 2.5 MPa and in a temperature range of 80-125° C. Many suitable variants of the LPO process are known, and several are disclosed in WO 2005/095315, WO 2005/095547, WO 2005/028404 and WO 2005/028407.

The catalytic hydrogenation step is preferably carried out at a temperature in the range of from about 150° C. to about 280° C., preferably from about 170° C. to about 240° C. The preferred pressure of operation is in the 20-300 atm range.

It has been found that the hydrogenation reaction to the desired alcohol enriched product mixture proceeds satisfactorily at a space velocity of from 0.2-2 vol/vol/hour, with the more preferred-space-velocity range being from 0.75-1.25 vol/vol/hour. By space velocity is meant the hourly flow by volume of the liquid reactants per unit volume of catalyst employed. The traditional hydrogenation catalysts may be employed such as the so-called copper chrome (also termed Cu/Cr or copper-chromium oxide or copper-chromite) catalysts and supported nickel. In an embodiment, recent advances in oxonation and/or hydrogenation, such as described in the aforementioned WO 2005058787 A1 and WO 2005058782 A1, may be employed, such as the use of sulphur tolerant regenerable catalysts, e.g., cobalt/molybdenum, sulphided nickel/molybdenum, nickel/tungsten sulphided derivatives used in the hydrogenation step of the process.

The above recited process parameters with regard to temperature, pressure, ratio of reactants, space velocity, and the like, are provided as guidance for one of ordinary skill in the art in possession of the present disclosure and should not be taken as critical parameters of the present invention. "Suitable conditions" for hydroformylation and hydrogenation can be determined without more than routine experimentation and would be understood by one of skill in the art to be suitable for commercial and/or experimental purposes.

The product stream obtained from the hydrogenation step typically will have an aldehyde content of up to 1 wt %. It is this stream, comprising a mixture of aldehyde and alcohol, that is advantageously used to contact the acetal formation catalyst for, in an embodiment, elimination of aldehyde, or in another embodiment, formation of acetal, or in yet another embodiment, purification of alcohol, or in still yet another embodiment, the formation of unsaturated ethers, among other embodiment. It will be recognized by one of ordinary skill in the art in possession of the present disclosure that these embodiments may be combined so that various objects of the invention may be met, such as elimination of aldehyde and formation of acetals and/or unsaturated ethers.

In the present disclosure the term "acetal" will be understood to mean one or more acetals and/or hemi-acetals. By "heavy products" is meant compounds with molecular weight higher than the desired alcohols, e.g., products having a carbon number of 2(n+1) or 4(n+1) when e.g. an aldol dimerisation step is included, or 6(n+1) when e.g. an aldol trimerisation step is included, wherein n is the carbon number of the olefin, which typically is 2, 3 or 4 when an aldol step is included. Such heavier products, in preferred embodiments, will typically not be distilled off with the recovered alcohol in the final distillation step. This separation of higher carbon number byproducts from the product alcohol is particularly suitable with alcohols having at least 5 carbon atoms. It may be possible with normal and/or isobutanol, but than the distillation step may become more complex because the butanol may be more difficult to separate by distillation from a byproduct such as dibutyl ether.

Suitable catalyst to be used for formation of the acetal include those known to catalyze the acetal reaction, such as mentioned in the prior art. Catalysts include acid resin catalysts, such as Amberlyst™ A-15 available from Rohm and Haas, sulfated zirconia, H-montomorillonite clay, and heteropoly acids (HPA) supported on inorganic oxides are particularly suitable. Also suitable are catalysts such as Ni—Mo on alumina, and zeolites such as MCM 22. All of these catalysts are commercially available and/or synthesized by known methods.

In embodiments catalysts in the shape of conventional distillation structures, such as rings, saddles, and the like, may be used in the present invention. The catalytic material is preferably a component of a distillation system functioning as both a catalyst and distillation packing, i.e., a packing for a distillation column having both a distillation function and a catalytic function, such as described in U.S. Pat. No. 6,015,875 and references cited therein, and also US2006/0129000 A1 and DE 2625074.

The particulate catalyst material may be a powder, small irregular chunks or fragments, small beads and the like. The particular form of the catalytic material in the structure is not critical so long as sufficient surface area is provided to allow a reasonable reaction rate. The sizing of catalyst particles can be best determined for each catalytic material, since the porosity or available internal surface area will vary for different material and affect the activity of the catalytic material.

The reactants are alcohols and aldehydes, each of which may, independently, be linear, branched, or a mixture thereof.

The process is applicable to the production of alcohols from any linear or branched olefins which may be subjected to hydroformylation but is particularly suited to the hydroformylation of C2, C3 or C4-C16, especially C5 or C6-C12 olefins, for the production, respectively, of C3, C4 or C5-C17, and especially C6 or C7-C13 alcohols. Such alcohols comprise 2-ethyl hexanol, 2-propyl heptanol, isoheptanol, isooctanol, isononanol, isodecanol and isotridecanol. Alternatively, the process is applicable to the production of the lower Oxo alcohols, such as any of the named butanols, pentanols or mixtures thereof. Each of these alcohols may be further reacted to produce an ester derivative, such as an acetate, an acrylate or methacrylate, a benzoate, a phthalate, an adipate, a trimellitate, a terephthalate, or a cyclohexane mono- or di-carboxylate. Suitable esterification processes are disclosed in WO 2005/021482, WO 2006/125670 or copending applications U.S. Ser. No. 60/906797 or U.S. Ser. No. 60/906732. If the ester is a benzoate or a phthalate, the ester may be further hydrogenated to produce respectively the cyclohexane mono- or di-carboxylate. Suitable hydrogenation processes are disclosed in EP 1042273, US 2004/0260113 or WO 2004/046078. The present invention is therefore particularly useful in the production of n-butyl acetate, n-butyl acrylate, n-pentyl acetate, n-pentyl acrylate, isononyl- or isodecyl benzoate (NB or IDB), di-isononyl phthalate (DINP) or cyclohexane dicarboxylate (DINDCH), di-isodecyl phthalate (DIDP) or cyclohexanoate (DIDCH). The method according to the invention therefore may further comprise the step (iv) of reacting a synthesis gas comprising carbon monoxide and hydrogen and at least one $C_nH_{2n}$ olefin in the presence of a hydroformylation catalyst under conditions suitable to obtain a product comprising an aldehyde containing n+1 carbon atoms, wherein n is from 3 to 12, and hydrogenating at least part of the aldehyde obtained in step (iv) in step (i). In a further embodiment of the invention, the first mixture comprises at least one $C_nH_{2n+2}$ paraffin and/or at least one $C_nH_{2n}$ olefin, wherein n is from 3 to 12, and whereby the contacting in step (ii) is performed in a first catalytic distillation tower comprising the acetal formation catalyst and under conditions suitable for the formation of the acetal or hemiacetal of the alcohol and the aldehyde and simultaneous carrying out distillation so that paraffin, water, and/or olefin are taken as overhead and alcohol, acetal and/or hemiacetal, and optionally unsaturated ethers are taken off as bottoms, which bottoms is passed to step (iii).

In another embodiment of the invention, step (ii) comprises a step of passing the second mixture over a second acetal formation catalyst and then separating the alcohol and the acetal and/or the unsaturated ether in a distillation column according to steo (iii).

In a further embodiment of the invention, the alcohol is selected from the group consisting of n-butanol, isobutanol, mixtures of C4 alcohols, n-pentanol, 2-methyl-butanol, 3-methyl butanol, mixtures of at least two C5 alcohols, 2-ethyl-pentanol, 2-ethyl hexanol, 2,4-dimethyl heptanol, and 2-propyl heptanol.

The invention may further include that the alcohol is further esterified to produce an ester, which optionally is an acetate, an acrylate, a methacrylate, a phthalate, a benzoate, a cyclohexane dicarboxylate, a trimellitate or an adipate.

In a further embodiment of the invention, the ester is a benzoate or a phthalate and the ester is further hydrogenated to produce a cyclohexane mono- or di-carboxylate.

The process is also applicable to the production of unsaturated ethers, particularly those in the range of C14-C26 or double the alcohol number of carbons, such as dibutyl or more particularly dipentyl ether from respectively any of the butanols or pentanols discussed above.

The process is also applicable to the production of acetals and/or hemi-acetals from the same product stream as for the above processes and also to the production of a combination of at least two of the products selected from the group consisting of alcohols, ethers, esters, and acetals.

The invention will be better understood by reference to the following description, which refers to the accompanying figures.

The accompanying figures, which are schematic representations of various embodiments of the invention, will be understood by one of skill in the art to be embodiments of the invention, illustrative thereof rather than limiting, and that numerous other configurations are possible within the scope of the present disclosure, including the appended claims. Likewise, it will be understood by one of skill in the art that certain details of the apparatus are not shown for convenience of view, such as pumps, exchangers, drums, valves, flow meters, temperature sensors, and the like, which are within the skill of the routine artisan to provide.

In FIG. 1, a crude stream 1 comprising alcohol and aldehyde enters first distillation tower 2, which may be a conventional distillation tower comprising standard distillation structures such as inert packing, bubble cap trays, sieve trays, and the like. In the distillation column the stream is separated by distillation, with paraffins and uncoverted olefins being removed as overheads 3 and a stream comprising concentrated alcohol and aldehyde removed as bottoms product in flow line 4. The bottoms product, comprising a concentrated mixture of alcohol and aldehyde, is sent to a separate aldehyde elimination reactor 5 comprising catalyst section 6, where residual aldehyde is converted to the acetal product and other heavy reaction products such as ethers. The alcohol and heavy product is sent through flow line 7 to alcohol recovery tower 8, and separated into the desired alcohol overheads 9 (also comprising water), and heavy bottoms fraction, removed from the tower through flow line 10. Distillation tower 8 may also be a conventional distillation tower comprising standard distillation structure such as inert packing, bubble cap trays, sieve trays, and the like.

In an embodiment, an aldehyde elimination reactor 5 comprising catalyst section 6 may be positioned upstream of first distillation tower 2 rather than between distillation towers 2 and 8, or two aldehyde elimination reactors may be used, one upstream of first distillation tower 2 and one between the two distillation towers. Other configurations of multiple aldehyde elimination reactors may be used, such as in series or in parallel.

Referring to FIG. 2, crude stream 21 comprising alcohol and aldehyde enters first catalytic distillation tower 22 comprising catalyst 26. Paraffin, water and uncoverted olefin are taken as overhead 23 with alcohol and heavy products taken as bottoms through line 24. The bottoms product is sent to alcohol tower 28 and distilled to provide overhead product 29 and bottoms product 30.

Referring to FIG. 3, crude stream 41 comprising alcohol and aldehyde enters the divided wall, catalytic distillation tower 44. Tower 44 structurally has wall 42 separating columns 47 and 48. Crude stream 41 enters into the tower side 47 which contains one or plural catalytic distillation features, which in this embodiment are represented by elements 46a and 46b. Product alcohol is taken off on sidestream 49 from tower side 48. Overheads 43 comprises paraffin, water, and unconverted olefins and the heavy fraction is taken as bottoms product through line 50.

The method according to the invention may further include that the first mixture comprises at least one $C_nH_{2n+2}$ paraffin and/or at least one $C_nH_{2n}$ olefin, wherein n is from 3 to 12, and whereby the contacting in step (ii) is performed in a first catalytic distillation tower comprising the acetal formation catalyst and under conditions suitable for the formation of the acetal or hemiacetal of the alcohol and the aldehyde and simultaneous carrying out distillation so that paraffin, water, and/or olefin are taken as overhead and alcohol, acetal and/or hemiacetal, and optionally unsaturated ethers are taken off as bottoms, which bottoms is passed to step (iii). This embodiment has the advantage that the water formed as byproduct from the formation of the acetal and/or hemiacetal and/or unsaturated ether is separated with the paraffin and/or olefin, and the risk for contaminating the product alcohol with water is reduced.

In a variant to the method of the invention, the first mixture is passed to a divided wall distillation tower comprising an inlet for the first mixture, a first vertical section containing acetal formation catalyst and a second vertical section comprising distillation packing and/or distillation trays, the first and second vertical section segregated by a vertical wall extending a predetermined distance from above the inlet to below the inlet for the first mixture, wherein the first mixture and the acetal formation catalyst are contacted under conditions suitable for the formation of the acetal of the alcohol and the aldehyde and simultaneous carrying out distillation so that an overheads is taken comprising the paraffin and/or the olefin, the alcohol is taken as a sidestream, and the acetal and optionally unsaturated ethers are taken off as bottoms. Also this variant offers the advantage of a reduced risk for contaminating the alcohol product with the water byproduct from the condensation reaction of the aldehyde with the alcohol.

In another embodiment of the invention, in the system provided by the invention the aldehyde elimination reactor is located downstream of the first distillation tower and fluidly connected to the bottoms thereof.

The system according to the invention may further comprise a second distillation tower located downstream of the aldehyde elimination reactor and fluidly connected thereto.

In another embodiment of the system provided by the invention, the aldehyde elimination reactor is located within the first distillation tower and below the inlet to this distillation tower.

In yet another embodiment of the system according to the invention, the first distillation tower is a divided wall distillation tower comprising a first vertical section containing the inlet and the aldehyde elimination reactor, and a second vertical section consisting essentially of distillation packing and/or distillation trays, the first and second vertical section segregated by a vertical wall extending a predetermined distance from above the tower inlet to below the inlet.

The invention may also be better understood by reference to the following example. As with reference to the above-described figures, the example should be taken as an embodiment intended to be illustrative of the invention rather than limiting, and one of ordinary skill in the art in possession of the present disclosure would understand that numerous other processes are possible within the scope of the present disclosure, including the appended claims.

A 250 g solution containing 2.3 wt. % octyl aldehyde (99% pure aldehyde, primarily consisting of n-octyl aldehyde, Aldrich) in 1-octanol ($\geq$99%, Aldrich) was added to a three-neck round bottomed flask resulting in an initial carbonyl number of ~10 g KOH/mg. In some experiments, ~25 g of MolSiv™ (drying agent available from UOP) was then added to the stirring solution to adsorb product water and drive the equilibrium of the reaction toward the production of acetal. In other experiments, no drying agent was used. The solution temperature was held at the desired value (indicated in the table below) before 2.5 g of catalyst was added (1 wt. % catalyst based on total solution mass). Samples (~2-4 mL) were drawn from the flask at regular time intervals and analyzed using a gas chromatograph. The high, initial concentration of octyl aldehyde was used so that its disappearance could be easily monitored via GC analysis.

For sulfated zirconia, amberlyst acid resin, and HPA catalysts, aldehyde conversions greater than 97% were achieved. For the H-Montmorillonite clay, aldehyde conversions greater than 93% were achieved. Times needed to complete reaction at these conversion percentages are listed in the table below:

| Catalyst | Drying agent used | No drying agent used |
|---|---|---|
| Amberlyst A-15 | 5 h (RT) | <1 h (RT) |
| 4.5% SO$_4$/ZrO$_2$ | 5 h (100° C.) | 3 h (100° C.) |
| H-Montmorillonite clay | 7 h (100° C.) | <1 h (100° C.) |
| HPA | <1 h (100° C.) | <1 h (100° C. |

These experiments indicate that the addition of a drying agent to the batch reaction slows down the reaction rate, and the removal of water favors the formation of acetals over unsaturated ethers. Water removal leads to very high acetal selectivity. Also, the absence of drying agent leads to faster rates and generally, more unsaturated ethers are formed. As more water is formed via the reaction, the reverse reaction between water and acetal begins leading to acetal decomposition giving off an alcohol and forming an unsaturated ether.

It is preferred that the selectivity of the reaction favors the formation of unsaturated ethers over acetal. In the formation of acetal, 1 mol of aldehyde reacts with 2 mol of alcohol. Since the alcohol is typically the desired product of the Oxo process, formation of acetal leads to a slight yield loss in desired product. However, in the formation of unsaturated ether, only 1 mol of alcohol is consumed and thus, the yield loss is less.

While the illustrative embodiments of the invention have been described with particularity, many variations will suggest themselves to those skilled in this art in light of the above detailed description. All such obvious variations are within the full intended scope of the appended claims, but the most preferred variations include: a method, which in an embodiment is a method for isolation and/or purification of an alcohol from a first mixture comprising an aldehyde and in excess of two equivalents of said alcohol but more generally is simply an elegant method for reacting alcohols and aldehydes, the improvement comprising contacting the first mixture (comprising the alcohol and aldehyde), typically an alcohol and aldehyde independently selected (although typically the range will be the same for the aldehyde and alcohol and typically it will be primarily a single carbon number) from alcohols and aldehyde in the carbon range of C3-C18, C4-C17, C5-C16, C6-C15, C7-C14, C8-C13, C9-C12, or any lower carbon number range listed to any higher carbon number range listed, with a acetal formation catalyst under conditions suitable for formation of the acetal of said aldehyde and said alcohol (which conditions may be readily determined by one of ordinary skill in the art in possession of the present disclosure and which in preferred embodiments would be commercially acceptable conditions) to produce a second mixture comprising said acetal and said alcohol, and distilling said second mixture to produce an overhead comprising said alcohol and a bottoms comprising at least one of said acetal and an unsaturated ether, which may be modified by one or more of the following preferred embodiments: (a) wherein said acetal formation catalyst is selected from at least one of acid resin catalysts, sulfated zirconia, H-montomorillonite clay, heteropoly acids (HPA) supported on inorganic oxides, Ni—Mo on alumina, and MCM 22; (b) including the steps of: (i) reacting a synthesis gas comprising carbon monoxide and hydrogen and at least one $C_nH_{2n}$ olefin in the presence of a hydroformylation catalyst under conditions suitable to obtain an aldehyde product containing n+1 carbon atoms, wherein n is from 4 to 12; then (ii) hydrogenating said aldehyde product to obtain said first mixture of at least one alcohol and residual aldehyde in the amount of from 0.05 to 2.0 wt %, based on the weight of said aldehyde product obtained in step (i); then (iii) contacting said first mixture with a acetal formation catalyst under conditions suitable for formation of the acetal of said aldehyde and said alcohol to produce a second mixture comprising said acetal, said alcohol, and at least one unsaturated ether, and then distilling said second mixture to produce an overhead comprising said alcohol and a bottoms comprising said acetal and/or said at least one unsaturated ether; including the steps of: (i) passing a stream comprising paraffins, at least one $C_nH_{2n}$ olefin, at least one alcohol having n+1 carbon atoms, and at least one aldehyde having n+1 carbon atoms, wherein n is from 4 to 12, to a first distillation tower wherein said stream is separated into an overhead comprising said paraffins and said at least one $C_nH_{2n}$ olefin, and a first bottoms comprising said at least one alcohol and said at least one aldehyde; then (ii) contacting said first bottoms with an acetal formation catalyst under conditions suitable for formation of the acetal and/or unsaturated ether of said aldehyde and said alcohol to produce said second mixture comprising said acetal and said alcohol; then (iii) passing said second mixture to an alcohol recovery tower and separating said second mixture into an overhead comprising said alcohol, and a second bottoms comprising said acetal, preferably wherein said second mixture further comprises unsaturated ethers and wherein said process further comprising a step of passing said second bottoms to a second distillation tower and separating said second bottoms into an overhead comprising said at least one unsaturated ether and a third bottoms comprising said acetal; including the steps of (i) contacting a stream comprising paraffins, at least one $C_nH_{2n}$ olefin, at least one alcohol having n+1 carbon atoms, and at least one aldehyde having n+1 carbon atoms, wherein n is from 4 to 12, with an acetal formation catalyst under conditions suitable for formation of the acetal of said aldehyde and said alcohol to produce said second mixture comprising said acetal, said alcohol, and at least one unsaturated ether; (ii) passing said second mixture to one or more distillation columns whereby said alcohol is separated from and said acetal and/or said unsaturated ether, optionally wherein step (ii) includes a step of passing a stream comprising said alcohol and said acetal over a second acetal formation catalyst and then separating said alcohol and said acetal in at least one distillation column; including the steps of: (i) passing a stream comprising paraffins, at least one $C_nH_{2n}$ olefin, at least one alcohol having n+1 carbon atoms, and at least one aldehyde having n+1 carbon atoms, wherein n is from 4 to 12, to a first catalytic distillation tower comprising an acetal formation catalyst; (ii) contacting said stream and said acetal formation catalyst under conditions suitable for the formation of the acetal of said alcohol and said aldehyde and simultaneous carrying out distillation so that paraffin, water, and unconverted olefin are taken as overhead and alcohol, acetal and optionally unsaturated ethers are taken off as bottoms; (iii) passing said bottoms product to an alcohol recovery tower wherein alcohol is taken as overhead and acetal and/or unsaturated ethers are taken as bottoms from said alcohol recovery tower; including the steps of: (i) passing a stream comprising paraffins, at least one $C_nH_{2n}$ olefin, at least one alcohol having n+1 carbon atoms, and at least one aldehyde having n+1 carbon atoms, wherein n is from 4 to 12, to a divided wall distillation tower comprising an inlet for said stream, a first vertical section containing acetal formation catalyst and a second vertical section comprising distillation packing and/or distillation trays, said first and second vertical section segregated by a vertical wall extending a predetermined distance from above said inlet to below said inlet said stream; (ii) contacting said stream and said acetal formation catalyst under conditions suitable for the formation of the acetal of said alcohol and said aldehyde and simultaneous carrying out distillation so an overhead comprising unconverted olefin is taken (and also generally paraffins and water), alcohol is taken as a sidestream, and said acetal and optionally unsaturated ethers are taken off as bottoms; and also in embodiments a system (generally an apparatus but also incorporatable into a method or process) comprising a hydrogenation reactor containing a catalyst effective for hydrogenating aldehydes to alcohols, a first distillation tower downstream of said hydrogenation apparatus, said first distillation tower having an inlet (generally an inlet for a stream comprising alcohol and aldehyde, recognizing that multiple inlets may be provided for separating species to be reacted), an outlet located substantially at or near the overhead of said tower and an outlet located substantially at or near the bottom of said tower (recognizing that under certain circumstances various sidestreams may also be provided for), and an "aldehyde elimination reactor" otherwise known as the acetal formation catalyst-containing reactor, wherein said aldehyde elimination reactor comprises distillation packing and/or trays and a catalyst effective for converting an aldehyde and an alcohol to the corresponding acetal, modifiable by one or more of the following preferred embodiments: wherein said aldehyde elimination reactor is downstream of said first distillation tower and fluidly connected to the bottoms thereof, particularly where there is further provided a second distillation tower is located downstream of said aldehyde elimination reactor and fluidly connected thereto; optionally wherein said aldehyde elimination reactor is located within said first distillation tower and below the inlet to said tower (in other words, to provide a catalytic distillation apparatus), and which in preferred embodiments further comprises a second distillation tower located downstream of said aldehyde elimination reactor and fluidly connected thereto; wherein said first distillation tower is a divided wall distillation tower comprising a first vertical section containing said inlet and said catalyst located below said inlet, and a second vertical section consisting essentially of distillation packing and/or distillation trays, said first and second vertical section segregated by a vertical wall extending a predetermined distance from above said inlet to below said inlet said stream, and which in preferred embodiments said vertical wall extends to include at least the portion of said first vertical section wherein said catalyst is located; and still another embodiment which is a method comprising contacting at least one alcohol and at least one aldehyde with a acetal formation catalyst under conditions suitable for formation of the acetal of said aldehyde and said alcohol to produce a mixture comprising said acetal, and then distilling said mixture to produce an overhead comprising said alcohol and a bottoms comprising at least one of the species selected from said acetal and an unsaturated ether; including one or more of the following preferred embodiments: wherein said distilling is in a catalytic distillation column containing said acetal formation catalyst; wherein said distilling occurs in an apparatus separate from and downstream from said acetal formation catalyst, optionally further comprising a step of distilling a first feedstream comprising olefins and said alcohol and said aldehyde to separate said olefins from a second feedstream comprising said alcohol and said aldehyde, then passing said second feedstream to said catalytic distillation column containing said acetal formation catalyst to produce said overhead and said bottoms; and in yet still another embodiment, there is a method comprising passing a product comprising aldehyde and alcohol (e.g., an Oxo product) to a first distillation tower to remove olefin (and typically paraffin), passing the bottoms (aldehyde, alcohol and typically heavies) to a hydrogenation apparatus (such as known in the art) to hydrogenated the aldehyde, taking this "hydro" product comprising residual aldehyde through a second distillation tower to separate off an olefin and paraffin still remaining and/or produced in the hydrogenation apparatus and then to a second tower to obtain the desired alcohol overhead and heavies as bottoms, wherein an acetal formation (aldehyde elimination) reactor is placed in at least one of the follow positions: (a) after the hydrogenation apparatus and before the second tower; (b) inside the second tower so that the second tower becomes a catalytic distillation tower such as described herein; (c) between the second and third towers; (d) or a combination thereof.

Trade names used herein are indicated by a ™ symbol or ® symbol, indicating that the names may be protected by certain trademark rights, e.g., they may be registered trademarks in various jurisdictions.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

The invention claimed is:

1. A system comprising a hydrogenation reactor containing a catalyst effective for hydrogenating aldehydes to alcohols, a first distillation tower downstream of the hydrogenation reactor, the first distillation tower having an inlet, an outlet located substantially at or near the overhead of the tower and an outlet located substantially at or near the bottom of the tower, and an aldehyde elimination reactor, wherein the aldehyde elimination reactor comprises distillation packing and/or trays and a catalyst effective for converting an aldehyde and an alcohol to the corresponding acetal.

2. The system according to claim 1, wherein the aldehyde elimination reactor is downstream of the first distillation tower and fluidly connected to the bottoms thereof.

3. The system according to claim 1, further comprising a second distillation tower located downstream of the aldehyde elimination reactor and fluidly connected thereto.

4. The system according to claim 1, wherein the aldehyde elimination reactor is located within the first distillation tower and below the inlet to this distillation tower.

5. The system according to claim 1, wherein the first distillation tower is a divided wall distillation tower comprising a first vertical section containing the inlet and the aldehyde elimination reactor, and a second vertical section consisting essentially of distillation packing and/or distillation trays, the first and second vertical section segregated by a vertical wall extending a predetermined distance from above the tower inlet to below the inlet.

6. A method for at least one of isolation and purification of an alcohol comprising the steps of
(i) catalytically hydrogenating an aldehyde containing stream to produce a first mixture comprising at most 2% wt of the aldehyde and at least 75% wt of the alcohol based on the weight of the total first mixture,
(ii) contacting the first mixture with an acetal formation catalyst under conditions suitable for formation of at least one of the acetal and an unsaturated ether of the aldehyde and the alcohol to produce a second mixture comprising the at least one of the acetal and the unsaturated ether and the alcohol, and
(iii) distilling the second mixture to produce an overhead comprising the alcohol and a first bottoms comprising the at least one of the acetal and the unsaturated ether.

7. The method of claim 6, wherein the acetal formation catalyst is selected from the group consisting of acid resin catalysts, sulfated zirconia, H- montomorillonite clay, heteropoly acids (HPA) supported on inorganic oxides, Ni—Mo on alumina, MCM 22, and combinations thereof.

8. The method of claim 6, further comprising:
(iv) reacting a synthesis gas comprising carbon monoxide and hydrogen and at least one $C_nH_{2n}$ olefin in the presence of a hydroformylation catalyst under conditions suitable to obtain a product comprising an aldehyde containing n+1 carbon atoms, wherein n is selected from 3 to 12, and hydrogenating at least part of the aldehyde obtained in step (iv) in step (i).

9. The method of claim 6, wherein the first mixture comprises at least one of a $C_nH_{2n+2}$ paraffin and a $C_nH_{2n}$ olefin, wherein n is selected from 3 to 12, and whereby the contacting in step (ii) is performed in a first catalytic distillation tower comprising the acetal formation catalyst and under conditions suitable for the formation of at least one of the acetal and the hemiacetal of the alcohol and the aldehyde and simultaneous carrying out distillation so that at least one of the paraffin, water, and the olefin are taken as overhead and at least one of the alcohol, the acetal and the hemiacetal are taken off as bottoms, which bottoms is passed to step (iii).

10. The method of claim 9, wherein also unsaturated ethers are taken off in said bottoms, which is passed to step (iii).

11. The method of claim 9, wherein the first mixture is passed to a divided wall distillation tower comprising an inlet for the first mixture, a first vertical section containing acetal formation catalyst and a second vertical section comprising at least one of distillation packing and distillation trays, the first and second vertical section segregated by a vertical wall extending a predetermined distance from above the inlet to below the inlet for the first mixture, wherein the first mixture and the acetal formation catalyst are contacted under conditions suitable for the formation of the acetal of the alcohol and the aldehyde and simultaneous carrying out distillation so that an overheads is taken comprising at least one of the paraffin and the olefin, the alcohol is taken as a sidestream, and the acetal are taken off as bottoms.

12. The method according to claim 6, wherein the alcohol is selected from the group consisting of n-butanol, isobutanol, mixtures of C4 alcohols, n- pentanol, 2-methyl-butanol, 3-methyl butanol, mixtures of at least two C5 alcohols, 2-ethyl-pentanol, 2-ethyl hexanol, 2,4-dimethyl heptanol, and 2-propyl heptanol, and mixtures thereof.

13. The method according to claim 6, wherein the alcohol is further esterified to produce an ester.

14. The method according to claim 13, wherein the ester is selected from an acetate, an acrylate, a methacrylate, a phthalate, a benzoate, a cyclohexane dicarboxylate, a trimellitate and an adipate, or mixtures thereof.

15. The method according to claim 13, wherein the ester is at least one of a benzoate and a phthalate and wherein the ester is further hydrogenated to produce at least one of a cyclohexane mono-carboxylate and a cyclohexane di-carboxylate.

16. A system comprising a hydrogenation reactor containing a catalyst effective for hydrogenating aldehydes to alcohols, a first distillation tower downstream of the hydrogenation reactor, the first distillation tower having an inlet, an outlet located at a location selected from substantially at and near the overhead of the tower and an outlet located at a location selected from substantially at and near the bottom of the tower, and an aldehyde elimination reactor, wherein the aldehyde elimination reactor comprises at least one of distillation packing and trays and a catalyst effective for converting an aldehyde and an alcohol to the corresponding acetal.

17. The system according to claim 3, wherein the aldehyde elimination reactor is downstream of the first distillation tower and fluidly connected to the bottoms thereof.

18. The system according to claim 3, further comprising a second distillation tower located downstream of the aldehyde elimination reactor and fluidly connected thereto.

19. The system according to claim 3, wherein the aldehyde elimination reactor is located within the first distillation tower and below the inlet to this distillation tower.

20. The system according to claim 3, wherein the first distillation tower is a divided wall distillation tower comprising a first vertical section containing the inlet and the aldehyde elimination reactor, and a second vertical section consisting essentially of at least one of distillation packing and distillation trays, the first and second vertical section segregated by a vertical wall extending a predetermined distance from above the tower inlet to below the inlet.

* * * * *